United States Patent
Huang

(10) Patent No.: US 8,426,196 B2
(45) Date of Patent: Apr. 23, 2013

(54) METHOD FOR REGULATING PROLIFERATION OF CELLS

(76) Inventor: Lynn L. H. Huang, Tainan (TW)

( * ) Notice: Subject to any disclaimer, the term of this patent is extended or adjusted under 35 U.S.C. 154(b) by 1052 days.

(21) Appl. No.: 12/155,488

(22) Filed: Jun. 5, 2008

(65) Prior Publication Data

US 2009/0305416 A1 Dec. 10, 2009

(51) Int. Cl.
*C12N 5/00* (2006.01)
*C12N 5/02* (2006.01)

(52) U.S. Cl.
USPC ............... 435/325; 435/402; 435/404

(58) Field of Classification Search .......... None
See application file for complete search history.

(56) References Cited

U.S. PATENT DOCUMENTS

| | | | |
|---|---|---|---|
| 6,129,956 A | 10/2000 | Morra et al. | |
| 6,339,074 B1 * | 1/2002 | Cialdi et al. | 514/54 |
| 8,017,394 B2 * | 9/2011 | Adkisson et al. | 435/377 |
| 2008/0248570 A1 * | 10/2008 | Turner et al. | 435/377 |
| 2009/0123430 A1 * | 5/2009 | De Sousa | 424/93.7 |

OTHER PUBLICATIONS

Heins et al., Stem Cells, 22: 367-376 (2004).*
Susan K. Nilsson, et al, "Hyaluronan is synthesized by primitive hemopoietic cells, participates in their lodgment at the endosteum following transplantation, and is involved in the regulation of their proliferation and differentiation in vitro", Blood, Feb. 1, 2003; vol. 101, No. 3, pp. 856-862.
Rei Ogawa, et al., "Osteogenic and chondrogenic differentiation by adipose-derived stem cells harvested from GFP transgenic mice", Biochem. Biophys. Res. Commun.; 313, 2004, pp. 871-877.
Rei Ogawa, et al., "Adipogenic differentiation by adipose-derived stem cells harvested from GFP transgenic mice-including relationship of sex differences", Biochem. Biophys. Res. Commun.; 313, 2004, pp. 511-517.

* cited by examiner

*Primary Examiner* — Daniel C Gamett
(74) *Attorney, Agent, or Firm* — Andrews Kurth LLP

(57) ABSTRACT

A method for regulating proliferation of cells, has steps of providing a first culture system with a surface that is coated with a biological material; inoculating and culturing cells on the surface of the first culture system in an appropriate medium, such that the proliferation of the cells is preserved; collecting the cells; providing a second culture system with a surface; and inoculating and culturing the cells on the surface of the second culture system in a culture medium containing the biological material, such that the proliferation of the cells is promoted. A method for regulating proliferation of cells is also provided, the method being the same as the previous method except that the step of inoculating and culturing in a first culture system is performed before the step of inoculating and culturing in a second culture system.

22 Claims, 3 Drawing Sheets

METHOD FOR REGULATING PROLIFERATION OF CELLS

BACKGROUND OF THE INVENTION

1. Field of the Invention

The present invention relates to a method for culturing cells. More specifically, it relates to a method for regulating proliferation of cells.

2. Description of the Prior Arts

Cell therapy is a prominently applied medical technique. Methods for culturing cells in vitro are essential to clinical cell therapy. Normal cells require essential nutrients and growth factors to grow in the in vitro culture, otherwise they will undergo cell death due to the absence of regulation by the natural physical environment. Therefore, culturing cells in vitro involves not only promotion of the propagation of cells but also inhibition of death and differentiation so as to maintain in an original state with same characteristics, especially to prevent differentiation in the in vitro culture before the cells are later transplanted to a recipient.

An extracellular matrix is found to be able to regulate growth of cells. Hyaluronan (HA) is one of significant extracellular components and is reported that it can affect the adhesion, migration, proliferation, cell fate of mesenchymal cells and the developmental ability of embryonic cells in vitro (S. K. Nilsson et al. (2003), *Blood*, 101:856-862; D. Peck and C. M. Isacke, (1996), *Curr. Biol.*, 6:5375-5385).

As the applicant knows, in the field of the art, there exist techniques either simply for promoting proliferation of cells in vitro with biological materials such as an extracellular matrix component or simply for preventing cell proliferation, differentiation and death in vitro with biological materials. There is a need for a method for regulating proliferation of cells by using a biological material to preserve and promote proliferation of cells as desired.

To overcome the shortcomings, the present invention provides a method for regulating proliferation of cells to mitigate or obviate the aforementioned problems.

SUMMARY OF THE INVENTION

According to the investigation of proliferation of cells being cultured under various conditions in vitro, a method for regulating proliferation of cells is found.

In one aspect, the present invention provides a method for regulating the proliferation of cells, which comprises steps of providing a first culture system with a surface that is coated with a biological material; inoculating and culturing cells on the surface of the first culture system in an appropriate medium, such that proliferation of the cells are preserved; collecting cells; providing a second culture system with a surface; and inoculating and culturing cells on the surface of the second culture system in a culture medium containing the biological material, such that the proliferation of the cells is promoted.

Preferably, the present invention also provides a method for regulating proliferation of cells, which comprises steps of providing a second culture system with a surface; inoculating and culturing cells on the surface of the second culture system in a culture medium containing a biological material, such that the proliferation of the cells is promoted; collecting the cells; providing a first culture system having a surface, wherein the surface is coated with the biological material; and inoculating and culturing the cells on the surface of the first culture system in an appropriate medium, such that the proliferation of the cells is preserved.

Preferably, the biological material is selected from the group consisting of hyaluronan, collagen, gelatin, fibronectin, elastin, laminin heparan sulfate, chondroitin, chondroitin sulfate, keratan, keratan sulfate, carrageenan, heparin, chitin, chitosan, alginate, agarose, agar, cellulose, methyl cellulose, carboxyl methyl cellulose, chitin, chitosan, glycogen and derivatives thereof.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
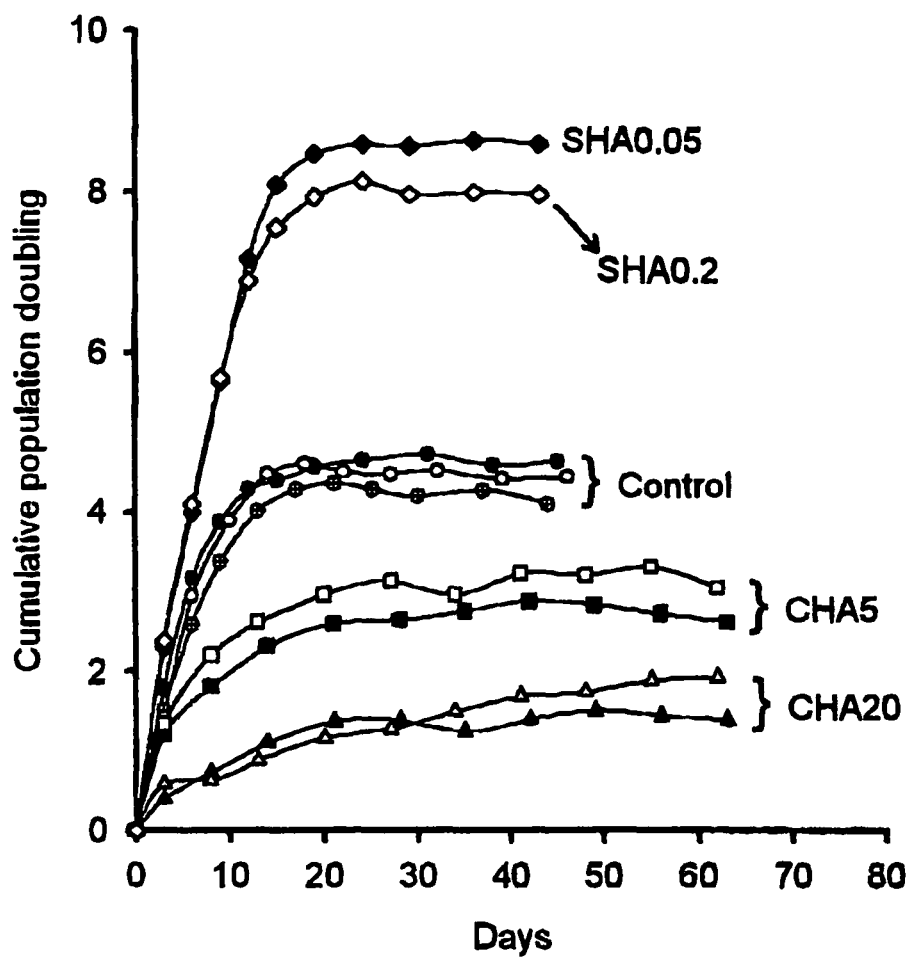
FIG. 1 illustrates a proliferative ate of mADSCs under various conditions.

According to the present invention, the method for regulating proliferation of cells comprises steps of: providing a first culture system with a surface that is coated with a biological material; inoculating and culturing cells on the surface of the first culture system in an appropriate medium, such that proliferation of the cells is preserved; collecting cells; providing a second culture system with a surface; and inoculating and culturing cells on the surface of the second culture system in a culture medium containing the biological material, such that the proliferation of the cells is promoted.

According to the present invention, the sequence of the steps presented in the method in accordance with the present invention does not at represent the sequence of the steps being carried out.

That is, in one preferred embodiment of the present invention, the steps in the method in accordance with the present invention are performed in a sequence as following:

(a) providing a first culture system having a surface, the surface being coated with an biological material;

(b) inoculating and culturing cells on the surface of the first culture system in an appropriate medium, such that proliferation of the cells is preserved;

(c) collecting the cells;

(d) providing a second culture system having a surface; and then (e) inoculating and culturing the cells on the surface of the second culture system in a culture medium containing the biological material, such that the proliferation of the cells is promoted.

In another preferred embodiment of the present invention, the steps in the method in accordance with the present invention are performed in a sequence as following:

(a) providing a second culture system having a surface;

(b) inoculating and culturing cells on the surface of the second culture system in a culture medium containing a biological material, such that proliferation of the cells is promoted;

(c) collecting the cells;

(d) providing a first culture system having a surface, wherein the surface is coated with the biological material; and then (e) inoculating and culturing the cells on the surface of the first culture system in an appropriate medium, such that the proliferation of the cells is preserved.

In another aspect, the method in accordance with the present invention further comprises steps of inoculating and culturing cells on the surface of the first culture system in an appropriate medium and collecting the cells, whereby the proliferation of the cells is further preserved for an extended period of time.

The term "preserving" or "preserved" as used herein refers to maintaining, conserving, saving, upholding, keeping, continuing, carrying on or sustaining, and in operation definition refers to slowing, or decreasing.

Based on the forgoing, the sequence of the steps of the method in accordance with the present invention can be determined as desired by a user for the purpose of regulating the proliferation of cells.

According to the present invention, the biological material is selected from the group consisting of proteinaceous extracelluar matrix component, polysaccharide and derivatives thereof.

According to the present invention, the biological material is selected from the group consisting of hyaluronan, collagen, gelatin, fibronectin, elastin, laminin, tenacin, vitronectin, polypeptides, heparan sulfate, chondroitin, chondroitin sulfate, keratan, keratan sulfate, carrageenan, heparin, chitin, chitosan, alginate, agarose, agar, cellulose, methyl cellulose, carboxyl methyl cellulose, glycogen and derivatives thereof.

Preferably, the biological material is selected from the group consisting of polysaccharide, sulfated polysaccharide and derivatives thereof.

More preferably, the biological material is selected from the group consisting of glycosaminoglycan, sulfated glycosaminoglycan and derivatives thereof.

More preferably, biological material is selected from the group consisting of hyaluronan, heparan sulfate, chondroitin sulfate, keratan sulfate, heparin, carrageenan, alginate, agarose, agar, cellulose, methyl cellulose, carboxyl methyl cellulose, glycogen and derivatives thereof.

Most preferably, the biological material is selected from the group consisting of hyaluronan and derivatives thereof.

As used herein, hyaluronan (also known as hyaluronic acid or hyaluronate) (HA) is a naturally occurring polymer of repeated disaccharide units of N-acetylglucosamine and D-glucuronic acid.

The hyaluronan derivatives are hyaluronic acid esters, crosslinked compounds of hyaluronic acid, hemiesters of succinic acid or heavy metal salts of the hemiester of succinic acid with hyaluronic acid or partial or total esters of hyaluronic acid, sulphated hyaluronic acid, N-sulphated hyaluronic acid, amines or diamines modified hyaluronic acid or derivatives thereof.

According to the present invention, the biological material has an average molecular weight in a range from 1 KDa to 20,000 KDa; and preferably in a range from 10 KDa to 15,000 KDa.

According to the present invention, the cells are obtained from a mammal such as bovine, porcine, murine equine, canine, feline, ovine, simian, and human. More particularly, the cells are obtained from human or murine.

According to the present invention, the cells are selected from the group consisting of stem cells, stromal cells, mesenchymal cells, tissue progenitor cells, blast cells, tissue-specialized cells and tumor cells.

Preferably, the cells are selected from the group consisting of adipose-derived stromal cells, placenta-derived stem cells and bone marrow-derived stem cells; alternatively, the cells are adipose-derived stromal cells, mesenchymal stem cells or fibroblasts.

According to the present invention, the first culture system has a surface, wherein the surface is coated with the biological material.

In a preferred embodiment of the method in accordance with the present invention, the first culture system comprises a culture carrier having a surface being coated with a biological material.

The term "culture carriers" as used herein refers to an element that can serve as a carrier or support during cell culture, and this term should not be construed in any limiting way.

According to the present invention, "culture carrier" should be understood as including, but not limited to, conventional culture vessels such as stirring flasks, stirred tank reactors, petri dishes, multiwell plates, microtiter plates, test tubes and culture flasks, cover glass, or the like. Such culture carriers are preferably formed of materials including, for example, polystyrene, polypropylene, acrylate polymers, nylon, nitrocellulose, sepharose, or the like.

The term "coating" and "coated" as used herein refer to applying a biological material to a surface of the culture carrier by known methods in the field of the art, for example, but not limited to, an application method, an immersion method, a crosslinking method or the like.

The application method includes applying a biological material aqueous solution to a surface of a culture carrier, optionally washing the surface with water and optionally drying the surface.

The immersion method includes adhering a biological material layer to a surface of the culture carrier by immersing the culture carrier in an aqueous solution of the biological material, and optionally washing the surface with water and then drying the surface. A concentration of the biological material aqueous solution used for these methods is not limited.

The crosslinking method includes applying a chemically activated biological material to a surface of a culture carrier, optionally washing the surface with water and optionally drying the surface; alternatively, a biological material is applied to a chemically activated surface of a culture carrier. Or both the biological material and the surface of a culture carrier are chemically activated while performing the coating procedure.

Particularly, methods disclosed in U.S. Pat. No. 6,129,956 for coating the surfaces of objects with hyaluronic acid, derivatives thereof or other natural or semisynthetic polymers can be utilized in the present invention for preparing a culture carrier having a surface coated with a biological material.

According to the present invention, the surface of the first culture system is coated with a biological material by a method comprising steps of: coating a surface of the culture carrier with a coating composition containing about 1 ng/mL to about 1 g/mL of the biological material; optionally incubating the coating composition on the surface of the culture carrier, and drying the culture carrier with the coating composition thereon.

According to the present invention, the coating composition containing about 1 ng/mL to about 1 g/mL of the biological material is prepared by dissolving the biological material in an appropriate solvent. Particularly, the appropriate solvent is an aqueous solvent, such as water, saline or the like.

Preferably, the surface of the first culture system is coated with the biological material in an amount from about 1 ng/cm² to 200 mg/cm²; more preferably, about 0.01 µg/cm² to 10 mg/cm²; and most preferably, about 0.5 µg/cm to 200 µg/cm².

According to the present invention, the appropriate medium is any known culture medium in the field of the art that is suitable for culturing undifferentiated cells according to the present invention. For example, the culture medium may include, but is not limited to, Dulbecco's modified Eagle's medium (DMEM), Eagle's minimal essential medium, RPMI, Media199, F-12 medium, William's medium E or the like. Preferably, the appropriate medium is any of the aforesaid culture medium supplemented with fetal bovine serum or the like. More preferably, the appropriate medium is essentially free of the biological material.

According to the present invention, the culture medium containing the biological material is any known medium in the field of the art that is suitable for culturing cells according to the present invention supplemented with the biological material. For example, the known medium in the field of the art may include, but not limited to, Dulbecco's modified Eagle's medium (DMEM), Eagle's minimal essential medium, RPMI, Media199, F-12 medium, William's medium E or the like.

Preferably, the culture medium is any of the aforesaid culture medium supplemented with fetal bovine serum or the like.

Preferably, the culture medium containing the biological material includes the biological material in an amount from about 0.1 ng/mL to 10 mg/mL.

More preferably, the culture medium containing the biological material includes the biological material in an amount from about 0.1 µg/mL to 1 mg/mL.

According to the present invention, the present invention may be employed for application in regenerative medicine, tissue-engineering, therapy using umbilical cord blood, peripheral blood, stem cells, tissue progenitor cells, tissue cells or the like for treating various target diseases. The target diseases are, for example, but not limited to, malignant tumor (such as leukemia, lymphoma or the like), genetic disease (such as cardiac disease or the like), autoimmune disease (such as multiple sclerosis, rheumatoid arthritis or the like) or tissue/organ loss (such as defects in skin, bone, cartilage, liver, neuron, brain, cornea, vessel, stomach, intestine, colon, sclera or the like).

In examples below, abbreviations further defined have following meanings. Abbreviations not defined have their generally accepted meanings, or meanings as defined above.

EXAMPLES

General Materials and Methods

1. Isolation and Culture of mADSCs mADSCs were isolated as previously described (R. Ogawa, et al., (2004), Supra.). Male FVB/IN mice were housed and raised at the National Cheng Kung University in Taiwan under standard conditions according to institutional guidelines for animal regulation. Briefly, inguinal fat pads from FVB/N mice were harvested, washed with phosphate buffered saline (GibcoBRL, Grand Island, USA), finely minced and digested with 0.1% collagenase (Worthington, Lakewood, USA) at 37° C. for 45 minutes. An equal volume of Dulbecco's modified Eagle's medium (DMEM, Gibco-BRL) containing 10% fetal bovine serum (PBS, Biological Industries, Israel) (her referred to DMEM-10% FBS) was added to the digest and the resulting solution was filtered through a 100-µm mesh, followed by centrifugation at 250×g for 10 minutes. The pellet was collected and resuspended in 160 mM $NH_4Cl$ (Sigma, USA) to lyse the red blood cells. After another centrifugation at 250×g for 10 minutes, the cell pellet was collected and resuspended in a conventional culture medium of DMEM-10% FBS containing 1% antibiotic/antimycotic solution or the same. The cell suspensions were then plated at $1\times10^4$ cells/cm² on a regular culture surface (control) or on HA pre-coated surface (CHA) and incubated at 37° C. with 5% $CO_2$. For a group of mADSCs cultured on regular culture surface, the culture medium DMEM-10% PBS contains 0.05 mg/mL or 0.2 mg/mL of HA (SHA0.05 or SHA0.2 respectively).

2. Isolation and Culture of Human Adipose-Derived Stromal Cells (hADSCs)

Waste adipose tissues were obtained from human adults by liposuction approved by the institutional review board according to the human tissue regulation. The obtained adipose tissues were usually contaminated with tissue fluid so as to form a mixture. The mixture were transferred to a 2-L beaker and stood till the adipose tissues floated above the mixture. The adipose tissues floated above the mixture were then collected to a 300-mL beaker and repeatedly washed with phosphate-buffered saline (PBS) (137 mM NaCl, 2.7 mM KCl, 10 mM $Na_2HPO_4.H_2O$, 2 mM $KH_2PO_4$, pH 7.4) until washed off solution was clear. The washed adipose tissues about 30 mL were treated with 9,000 IU collagenase in 20 mL HBSS-Ca buffer (5.4 mM KCl, 0.4 mM $KH_2PO_4$, 0.8 mM $MgSO_4.7H_2O$, 137 mM NaCl, 5.1 mM D-glucose, 0.4 mM $Na_2HPO_4$, 1 mM $CaCl_2.2H_2O$, 10 µg/mL gentamicine and 0.25 µg/mL fungizone) and agitated at 125 rpm in a waterbath at 37° C. for 1 hour with vigorously agitation every 20 to 30 minutes to obtain a digested solution. The digested solution was filtered sequentially through filter membranes with pore size of 500 µm, 100 µm and 37 µm to remove undigested tissues and to obtain a cell filtrate. The filtrate was collected in a 50-mL centrifuge tube, centrifuged at 800×g for 10 mins and resuspended in 5 mL DMEM (Dulbecco's Modified Eagle Medium) to obtain adipose derived stromal cells (hADSCs). The hADSCs were mixed with 15 mL RBC lysis buffer (155 mM $NH_4Cl$, 10 mM $KHCO_3$ and 0.1 mM EDTA) and centrifuged at 800×g for 10 mins to remove red blood cells. The cell pellet was then suspended in 20 mL DMEM with 10% FBS and the cell numbers were accessed by trypan blue staining and hemacytometer.

3. Isolation and Culture of Normal Human Dermal Fibroblasts (NHDFs)

Normal human dermal fibroblast (NHDFs) were purchased from Cloneties Co. (USA) The NHDFs were cultured in DMEM containing 10% FBS and plated at $1\times10^4$ cells/cm² on regular culture surface (control) or on HA pre-coated surface (CHA) and incubated at 37° C. with 5% $CO_2$.

4. Culturing Cells Under HA-Containing Conditions

I. Establishing CHA Culture System

CHA surface was prepared by coating HA on a regular culture surface and CHA5 as well as CHA20 were prepared by coating with 5 and 20 µg/cm² HA on surface. For preparing CHA5 and CHA20, 200 µL of 1 mg/mL hyaluronan solution was evenly applied to a well of a 24-well plate (Nunc Cat. No. 142475) which was positioned horizontally and prewarmed between 40° C. to 50° C. 190 µL and 160 µL of HA solution were respectively aspired leaving about 5 and 20 µg/cm² HA in each well of the 24-well plate after drying. The state of HA coating in the 24-well plate was further assured by staining with 1% w/v alcian blue in 3% w/v acetic acid. The plate was stored in a desiccator for later use.

II. Culturing Cells in Control and HA-Containing Culture Systems

Cells cultured with DMEM-10% FBS on regular culture surface were used as control. Two kinds of HA-containing culture system were applied: (A) SHA where cells were cultivated with DMEM-10% PBS containing HA (Mw=720 KDa, Pentapharm, Basel, Switzerland) at concentration of 0.2 mg/mL (SHA0.2) or 0.05 mg/mL (SHA0.05) on regular culture surface; (B) CHA where cells were cultivated with DMEM-10% FBS on HA pre-coated surfaces containing 5 µg/cm$^2$ (CHA5) or 20 µg/cm$^2$ (CHA20) of HA. Serial passages of cells cultured in control, SHA, and CHA were carried out when cells reached subconfluence. Cells were trypsinized, centrifuged and resuspended in an appropriate culture medium, DMEM-10% FBS for control and CHA groups; DMEM-10% FBS-SHA for SHA groups. The Cells were then plated at 1×10$^4$ cells/cm$^2$ in each group. The increase of population doubling (ΔPD) was calculated according to the formula of ΔPD=log (N$_f$/N$_0$)/log 2, where N$_f$ is the final number of cells at subconfluence, and N$_0$ is the initial number of plated cells.

Example 1

Altered Proliferative Behaviors of mADSCs in Response to HA

The present example investigated the proliferative behaviors of mADSCs upon different HA treatment by analyzing the increase of population doubling of the mADSCs.

The proliferative lifespan of mADSCs cultured in control, SHA (0.05 and 0.2 mg/mL) and CHA (5 and 20 µg/cm$^2$) culture system were evaluated by the method as described in "General materials and methods". The independent experiments were performed in control group, while two independent experiments were performed in each of SHA0.05, SHA0.2, CHA5 and CHA 20 groups.

Results:

The proliferative lifespans of mADSCs in various conditions were compared in FIG. 1. The growth rate of mADSCs of SHA0.05 and SHA0.2 group were significantly higher (*p<0.05 and **p<0.01 respectively at P5) tan that of the control group. Upon culturing on CHA, mADSCs exhibited a much more gradual growth profile and the proliferative lifespan seemed to be preserved.

Example 2

Regulating Proliferative Behaviors of hADSCs by HA Treatment

The present example involves regulating proliferative behaviors of hADSCs upon HA treatments in various sequences.

hADSCs were collected and cultured by the method as described in "General materials and methods", except the cells were subcultured for passages every three days and subjected to culturing under the following two schemes. The increase of population doubling of each group was counted and evaluated by methods as described above.

I. CHA-SHA Group:

hADSCs were initially cultured on CHA20 for 2 passages and then subcultured onto a SHA 0.2 culture system.

II. SHA-CHA Group:

hADSCs were initially cultured on a SHA 0.2 culture system for 2 passages and then subcultured onto CHA20 culture system.

Figure 2:
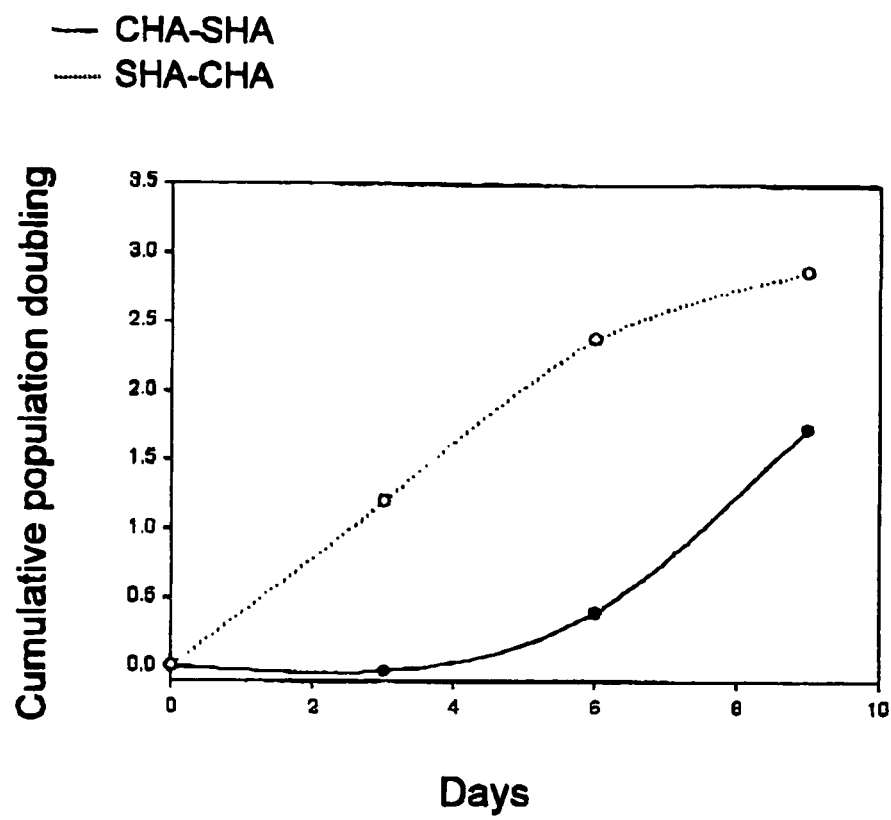
FIG. 2 illustrates proliferative lifespan of hADSCs cultured in CHA culture system in combination with SHA culture system in two different sequences.

Results:

As shown in FIG. 2, when hADSCs were cultured in CHA culture system, the increase of population doubling of hADSCs almost did not change. This indicated that hADSCs grow slowly in the CHA culture system. Once hADSCs cultured in CHA were subcultured to a SHA culture system, a remarkable progression in the increase of population doubling was observed. This demonstrates that hADSCs regain a faster proliferative rate upon their culture in the SHA culture system. On the contrary, hADSCs initially cultured in SHA culture system had a faster proliferative rate, and the increase of population doubling became preserved once hADSCs were subcultured to CHA culture system. This indicated that the proliferative rate of hADSCs slowed down upon their culturing in the CHA culture system. Therefore, the alternative application of CHA and SHA culture system on cells can effectively regulate proliferation of hADSCs in vitro.

Example 3

Regulating Proliferative Behaviors of NHDFs by HA Treatment

The present example involves regulating proliferative behaviors of NHDFs upon HA treatments in various sequences.

NHDFs were collected and cultured by the method as described in "General materials and methods", except the cells were subcultured for passages every three days and subjected to culturing under the following two schemes. The increase of population doubling of each group was counted and evaluated by methods as described above.

I. CHA-SHA Group:

NHDFs were initially cultured on CHA20 for 2 passages and then subcultured onto a SHA 0.2 culture system.

II. SHA-CHA Group:

NHDFs were initially cultured on a SHA 0.2 culture system for 2 passages and then subcultured onto CHA20 culture system.

Figure 3:
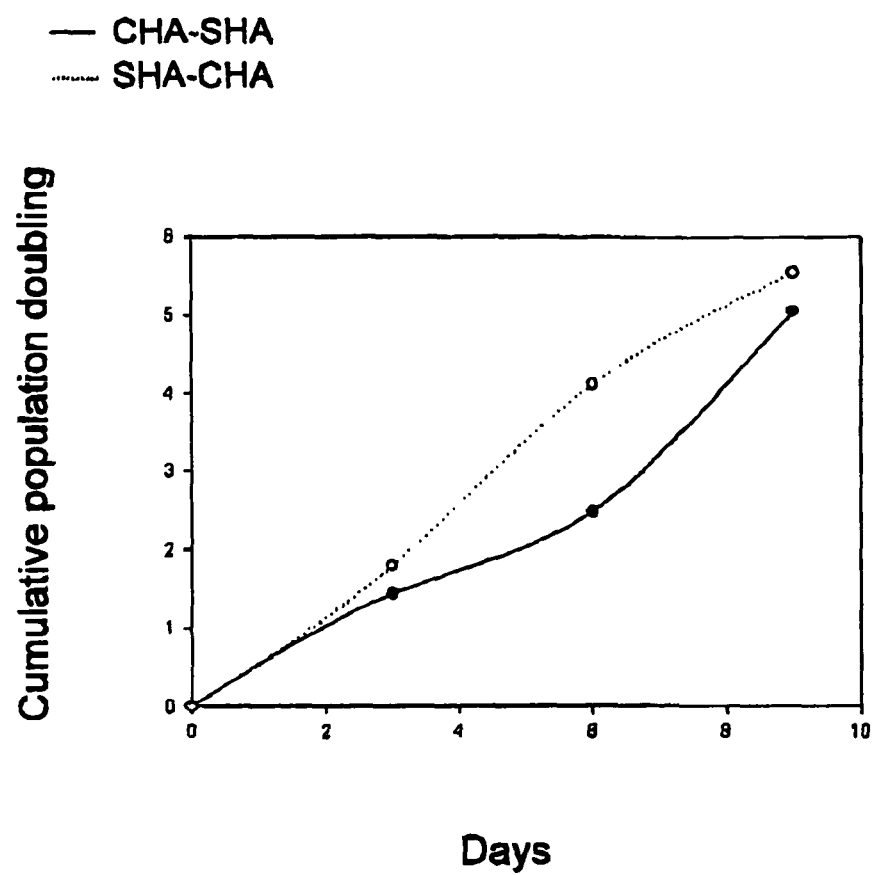
FIG. 3 illustrates proliferative lifespan of NHDFs cultured in CHA culture system in combination with SHA culture system in two different sequences.

Results:

As shown in FIG. 3, when NHDFs were cultured in CHA culture system, the increase of population doubling of NHDFs was slow. This indicated that NHDFs grow slowly in the CHA culture system. Once NHDFs cultured in CHA were subcultured to a SHA culture system, a remarkable progression in the increase of population doubling was observed. This demonstrates that NHDFs regain a faster proliferative rate upon their culture in the SHA culture system. On the contrary, NHDFs initially cultured in SHA culture system had a faster proliferative rate, and the increase of population doubling became gradual once NHDFs were subcultured to the CHA culture system. This indicated that the proliferative rate of NHDFs slowed down upon their culturing in the CHA culture system. Therefore, the alternative application of CHA and SHA culture system on cells can effectively regulate proliferation of NHDFs in vitro.

All patents, patent applications, and literature cited in the specification were incorporated by reference in their entirety. In the case of any inconsistencies, the present disclosure, including any definitions therein will prevail.

Even though numerous characterstics and advantages of the present invention have been set forth in the foregoing description, together with details of the structure and features of the invention, the disclosure is illustrative only. Changes may be made in the details within the principles of the invention to the full extent indicated by the broad general meaning of the terms in which the appended claims are expressed.

What is claimed is:

1. A method for regulating the rate of population doubling of cells comprising the following sequence of steps:
   (a) providing a first culture system with a surface that is coated with a biological material in an amount from about 0.1 ng/cm$^2$ to 200 mg/cm$^2$, wherein the biological material is selected from the group consisting of proteinaceous extracellular matrix component, polysaccharide, and derivatives thereof;
   (b) inoculating and culturing cells on the surface of the first culture system in an appropriate medium, such that the rate of population doubling of the cells is preserved;
   (c) collecting the cells;
   (d) providing a second culture system: and
   (e) inoculating and culturing the cells in the second culture system in a culture medium containing the biological material in an amount from about 0.1 ng/mL to 10 mg/mL, such that the rate of population doubling of the cells is increased.

2. The method according to claim 1, wherein the biological material is selected from the group consisting of hyaluronan, collagen, gelatin, fibronectin, elastin, laminin, heparan sulfate, chondroitin, chondroitin sulfate, keratan, keratan sulfate, carrageenan, heparin, chitin, chitosan, alginate, agarose, agar, cellulose, methyl cellulose, carboxyl methyl cellulose, glycogen, and derivatives thereof.

3. The method according to claim 1, wherein the biological material is selected from the group consisting of polysaccharide, sulfated polysaccharide, and derivatives thereof.

4. The method according to claim 3, wherein the biological material is selected from the group consisting of glycosaminoglycan, sulfated glycosaminoglycan, and derivatives thereof.

5. The method according to claim 4, wherein the biological material is selected from the group consisting of hyaluronan, heparan sulfate, chondroitin sulfate, keratan sulfate, heparin, and derivatives thereof.

6. The method according to claim 5, wherein the biological material is selected from the group consisting of hyaluronan and derivatives thereof.

7. The method according to claim 1, wherein the cells are selected from the group consisting of stem cells, tissue progenitor cells, blast cells, tissue-specialized cells and tumor cells.

8. The method according to claim 7, wherein the cells are selected from the group consisting of adipose-derived stromal cells, placenta-derived stem cells and bone marrow-derived stem cells.

9. The method according to claim 7, wherein the cells are fibroblasts.

10. The method according to claim 1, wherein the appropriate medium is essentially free of the biological material.

11. The method according to claim 10, wherein the surface of the second culture system is essentially free of the biological material.

12. A method for regulating the rate of population doubling of cells comprising the following sequence of steps:
   (a) providing a second culture system;
   (b) inoculating and culturing cells in the second culture system in a culture medium containing a biological material in an amount from about 0.1 ng/mL to 10 mg/mL, such that the rate of population doubling of the cells is increased;
   (c) collecting the cells;
   (d) providing a first culture system having a surface, wherein the surface is coated with the biological material in an amount from 0.1 ng/cm$^2$ to 200 mg/cm$^2$, wherein the biological material is selected from the group consisting of proteinaceous extracellular matrix component, polysaccharide, and derivatives thereof; and
   (e) inoculating and culturing the cells on the surface of the first culture system in an appropriate medium, such that the rate of population doubling of cells is preserved.

13. The method according to claim 12, wherein the biological material is selected from the group consisting of hyaluronan, collagen, gelatin, fibronectin, elastin, laminin, heparan sulfate, chondroitin, chondroitin sulfate, keratan, keratan sulfate, carrageenan, heparin, chitin, chitosan, alginate, and derivatives thereof.

14. The method according to claim 12, wherein the biological material is selected from the group consisting of polysaccharide, sulfated polysaccharide, and derivatives thereof.

15. The method according to claim 14, wherein the biological material is selected from the group consisting of glycosaminoglycan, sulfated glycosaminoglycan, and derivatives thereof.

16. The method according to claim 15, wherein the biological material is selected from the group consisting of hyaluronan, heparan sulfate, chondroitin sulfate, keratan sulfate, heparin, and derivatives thereof.

17. The method according to claim 16, wherein the biological material is selected from the group consisting of hyaluronan and derivatives thereof.

18. The method according to claim 12, wherein the cells are selected from the group consisting of stem cells, tissue progenitor cells, blast cells, tissue-specialized cells and tumor cells.

19. The method according to claim 18, wherein the cells are selected from the group consisting of adipose-derived stromal cells, placenta-derived stem cells and bone marrow-derived stromal cells.

20. The method according to claim 18, wherein the cells are fibroblasts.

21. The method according to claim 12, wherein the appropriate medium is essentially free of the biological material.

22. The method according to claim 21, wherein the surface of the second culture system is essentially free of the biological material.

* * * * *